United States Patent [19]

Molnar et al.

[11] 4,436,913

[45] Mar. 13, 1984

[54] 1H- AND 2H- INDAZOLE DERIVATIVES

[75] Inventors: Istvan Molnar; Kurt Thiele; Felix Geissmann; Ulrich Jahn, all of Zofingen, Switzerland

[73] Assignee: Siegfried Aktiengesellschaft, Zofingen, Switzerland

[21] Appl. No.: 375,116

[22] PCT Filed: Sep. 5, 1980

[86] PCT No.: PCT/EP80/00094

§ 371 Date: Apr. 28, 1982

§ 102(e) Date: Apr. 28, 1982

[87] PCT Pub. No.: WO82/00824

PCT Pub. Date: Mar. 18, 1982

[51] Int. Cl.³ .................................... C07D 403/12
[52] U.S. Cl. ........................... 548/316; 424/251; 424/273 R; 544/298; 544/320; 544/321; 544/331; 548/371; 548/372
[58] Field of Search ............... 548/316; 544/331, 320, 544/321, 298; 424/273 R, 251

[56] References Cited
U.S. PATENT DOCUMENTS 3,847,934 11/1974 Neumann ........................... 548/316
4,036,976 7/1977 Neumann ......................... 548/316 X

*Primary Examiner*—Richard A. Schwartz
*Attorney, Agent, or Firm*—Jordan and Hamburg

[57] ABSTRACT

1H- and 2H- indazole derivatives and pharmaceuticals containing these blood-pressure lowering 1H- and 2H-indazole derivatives of the formula

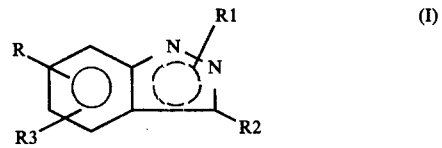

and their acid addition salts, wherein R1 may be in position 1 or position 2 on the nitrogen atoms in formula I. The groups R1, R2 and R3 represent hydrogen or the usual lower molecular groups. The R group is a 2-imidazolinylamino group or a 3,4,5,6-tetryhydropyrimidinylamino group, wherein these groups may also be present in their tautomeric forms. These groups may also be in an aryl group in the R1 group, in which case the R group may also be a halogen atom. R may only represent one of the heterocyclic secondary or tertiary amino groups in the 4 or 7 position for the 1H-indazole derivatives when the R1 group is simultaneously an aryl or an aralkyl group.

17 Claims, No Drawings

1H- AND 2H- INDAZOLE DERIVATIVES

SUMMARY OF THE INVENTION

This invention relates to 1H- and 2H-indazole derivatives of the formula

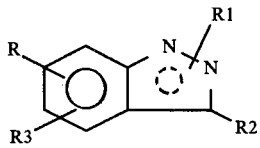

and their acid addition salts wherein formula I, R1 represents hydrogen, a lower alkyl, a lower aralkyl or an aryl group and is bound to one or both nitrogen atoms in the 1 or 2 position, wherein the aryl group and the aryl portion or the aralkyl group may be individually or multiply substituted, uniformly or differently, with a R4 group.

R2 and

R3 may be equal or different and represent hydrogen, halogen, an hydroxyl group, a lower alkyl group, a lower alkoxy group or a lower alkylthio group, and R4 and R, equal or different from each other, represent a halogen atom or one of the secondary or tertiary amino groups

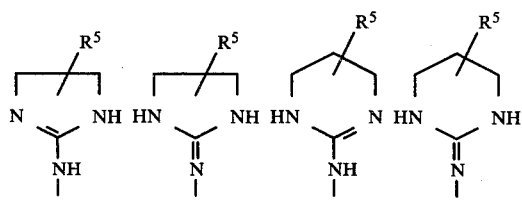

provided that at least one of the R or R4 groups is one of the aforementioned secondary or tertiary amino groups and R, in the 4 or 7 position, also represents one of the noted secondary or tertiary amino groups for the 1H-indazole derivatives only when the R1 group is simultaneously an aryl oraralkyl group, and wherein R5 represents hydrogen, an hydroxyl group or a lower alkyl or alkoxy group.

This invention further relates to the utilization of the aforementioned substances as active blood-pressure lowering substances for the manufacture of pharmaceuticals for animal and human medicine.

DETAILED DESCRIPTION OF THE PREFERRED EMBODIMENTS

The way of writing the indazole ring system in formula I means that the 1H-indazole derivatives

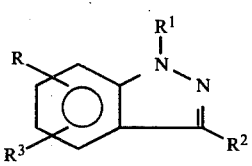

as well as the 2H-indazole derivatives

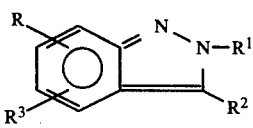

are to be understood by formula I.

The expression "lower" in combination with alkyl groups or alkyl portions in other groups, especially in the alkoxy and aralkyl groups, designates alkyl groups or alkyl portions with up to 6 carbon atoms, wherein these alkyls may also be cycloalkyls. Preferably, the expression "lower", in this connection, represents saturated, branched or unbranched acyclical carbon groups with up to 4 carbon atoms total.

Of course, only pharmacologically acceptable acid addition salts, especially hydrochlorides and nitrates, are employed in the manufacture of medicines.

Tautomerism is observed with respect to the R group for the 2-imidazolin-2-yl-derivatives and the imidazolidine derivatives as well as for the 3,4,5,6-tetrahydropyrimidine derivatives and the hexahydropyrimidine derivatives.

The R group is preferably a 2-imidazolin-2-yl-amino group (or its tautomers) or a chlorine atom, wherein in the latter case, the R4 group may be a 2-imidazolin-2-yl-phenyl- or -benzyl group that may be additionally substituted by chlorine. The R1 group is preferably a methyl group or possibly a substituted benzyl group, while the R2 and R3 groups preferably each represent one hydrogen atom.

The following substances and their addition salts have special significance: 6-(2-imidazolin-2-yl-amino)-1-methyl-1H-indazole, 4-(2-imidazolin-2-yl-amino)-2-methyl-2H-indazole, 4-(2-imidazolin-2-yl-amino)-2-benzyl-2H-indazole and 5-(2-imidazolin-2-yl-amino)-1-methyl-1H-indazole.

The indazoles of formula I can be produced by many different processes.

One method for producing the indazoles of formula I, when R is not a halogen, is characterized in that a correspondingly substituted indazole, which carries an amino group in the position of the benzene ring into which the R group is to be introduced, is condensed with a compound of the formula

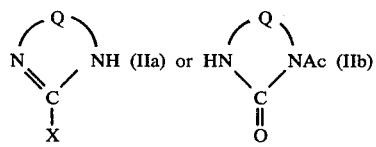

wherein X is a group that is splittable with hydrogen under condensation conditions, preferably a halogen, especially chlorine, and Ac is an acyl group, especially a lower alkyl acyl group or a substituted or unsubstituted phenyl acyl group. Q represents an ethylene or propylene group herein.

If a compound of formula IIa is used as a starting substance for this condensation, then such substance is preferably introduced in the form of a free base in the presence of a polar or non-polar solvent. Alcohols, ether or chlorinated hydrocarbons serve as solvents. Condensation proceeds in a temperature range between room temperature and about 150° C. The precipitated product, in the form of a salt, is separated and worked up.

When substituent X in formula IIa is an alkylthio group or a nitroamino group, then the substance of formula IIa is preferably introduced in the form of a salt, condensation in methanol or ethanol proceeding at increased temperature.

When condensation proceeds with a substance of formula IIb, then the process may be especially carried out in a solution or suspension of the amine, preferably POCl$_3$. Condensation proceeds at increased temperature, especially when using POCl$_3$ at temperatures up to the boiling point of the POCl$_3$. The acetyl compound of the end product is obtained herein, which is then converted in acetic acid or methanol into the compound of formula I.

A second method for the manufacture of the substances of formula I is distinguished by in situ formation of the imidazoline, imidazolidine or the pyrimidine ring. In this method, a diamine of the formula H$_2$N—Q—NH$_2$, in which Q may represent the ethylene or propylene group, as a free base or in the form of a monoacid addition salt, is reacted with a corresponding substituted indazole, which in the position in which the R group is to be introduced, may either represent a cyanoamino group, or a group of formula (III)

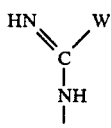
(III)

in which W, under condensation conditions, represents a splittable alkylthio group, an alkoxy group, an amino group or nitroamino group, or has a —N=C(Hal)$_2$ group, wherein Hal represents a halogen atom. In the manufacture of the imidazoline and tetrahydropyrimidine derivatives by this method, the indazole ring system preferably has at the position in which the substituent R is to be introduced, an isothiuroniumamino group of the formula (IV)

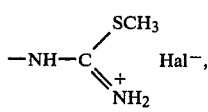
(IV)

in which the halide is preferably an iodide. When this substituent is especially the isothiuroniumiodidamino group, the ring closure condensation is effected in an inert solvent, for example in methanol or dioxane in a temperature range between about 40° to 210° C. When the substituent in the indazole ring system is a cyanoamino group, the reaction is effected in aliphatic alcohols, ether or aliphatic hydrocarbons at increased temperatures in a range between about 60° to 220° C.

The reaction products obtained by one of these processing variants can be separated in the usual manner and purified by re-crystallization.

According to a third method, when the R group represents one of the secondary or tertiary amino groups, it may be subsequently introduced in a way such that the group of formula (V)

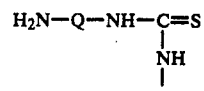
(V)

is initially introduced at the position of the indazole ring intended for R, wherein the sulfur may also be replaced in this group by an oxygen atom, and Q may also represent the ethylene or propylene group, on which the ring closure condensation is then effected. The reaction preferably proceeds in a polar solvent, for example dimethylformamide, methanol, ethanol or water, at moderately high temperatures in a range from about 30° to 160° C., in the presence of basic substances, such as, for example, alkali metal hydroxides.

The starting substances necessary to execute the preceding methods for manufacture of the substances of the formula I are either available on the market or can be produced by methods described in the pertinent technical literature.

The invention is illustrated in more detail in the following examples of embodiments.

EXAMPLE 1

6-(2-Imidazolin-2-yl-amino)-1-methyl-indazole hydrochloride

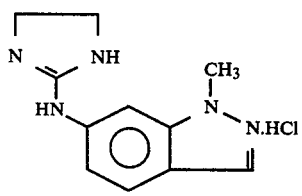

10 g 2-chloro-imidazoline hydrogen sulfate is dissolved in 50 ml 2 n NaOH. The free base is then extracted with methylene chloride. The solvent is then partially distilled, the residue being treated with ether. The resultant solution is dissolved in 4.5 g 6-amino-1-methyl-indazole, and treated in 130 ml abs. THF. The mixture is stirred for 60 hours at room temperature. The product separates herein in solid form. The precipitated product is filtered and washed with ether. After recrystallization from absolute ethanol, the hydrochloride of the product has a melting point between 247° to 249° C. Elementary analysis for C$_{11}$H$_{14}$N$_5$Cl (MW 251.7):

|  | C (%) | H (%) | N (%) | Cl (%) |
| --- | --- | --- | --- | --- |
| Calculated | 52.49 | 5.61 | 27.82 | 14.08 |
| Found | 52,59 | 5.70 | 27.76 | 14.16 |

EXAMPLE 2

4-(2-Imidazolin-2-yl-amino)-2-methyl-indazole hydrochloride

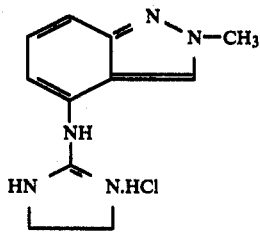

4 g 4-amino-2-methyl-indazole is dissolved in 120 ml THF. The solution is treated with a solution of 2-chloro-imidazoline base, which is prepared from 10 g 2-chloro-imidazoline sulfate (prepared according to J. Heteroc. Chem. 11, 258) with 2 n NaOH in methylene chloride.

After three days of standing at 20° C., the hydrochloride product has completely precipitated. The product is filtered and recrystallized from isopropanol. The recrystallized hydrochloride has a melting point from 270° to 271° C., obtained with a yield of 60%.

EXAMPLE 3

4-(2-Imidazolin-2-yl-amino)-2-benzyl-indazole

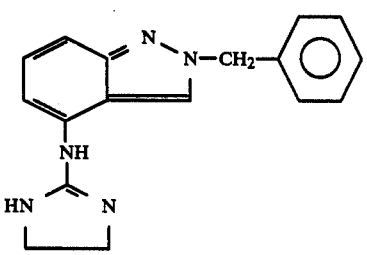

(A) 6.9 g 4-amino-2-benzyl-indazole is dissolved in 100 ml absolute THF. The solution is treated with a solution of 6.5 g chloroimidazoline in 100 ml absolute THF. The reaction product is subsequently stirred for 38 hours in a darkened, sealed flask at room temperature. The reaction product herein precipitates out as a white precipitate. After decantaion, the residue is dissolved in 50 ml water, alkalyzed with 2 n NaOH and extracted three times, in each instance with 100 ml ethyl acetate. The extracts are combined and washed three times, in each instance with 50 ml water. Next, they are dried over sodium sulfate and concentrated to a volume of about 20 ml. A white, crystalline substance is obtained herein, which is separated and recrystallized from a mixture of ethyl acetate and methanol. 1.3 g purified white crystalline product having a melting point from 214° to 216° C. is obtained.

(B) 15.2 g S-methyl-N-(2-benzyl-indazole-4-yl)-isothiuronium-iodide is dissolved in 155 ml methanol and treated with 3.2 ml ethylene diamine. The mixture is kept for 20 hours under reflux at boiling temperature. The residue obtained is dissolved in 50 ml hot, aqueous 2 n HCl. After filtration, the solution is treated with 2 n NaOH and extracted three times, in each instance with 100 ml chloroform. The combined extracts are washed with water, dried over sodium sulfate and concentrated. The crystalline, white residue is separated and recrystallized from a mixture of methanol and acetic ester. 5.06 g purified, white, crystalline end product is obtained herein, with a melting point lying between 214° and 216° C.

EXAMPLE 4

5-(2-imidazolin-2-yl-amino)-1-methyl-indazole hydrochloride

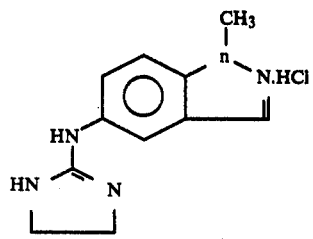

5-amino-1-methyl-indazole is dissolved in absolute THF and treated with a solution of an equimolar quantity of 2-chloro-imidazoline in ether. The mixture is stirred for 48 hours in a darkened, sealed flask at room temperature. The precipitated reaction product is separated and recrystallized from ethanol. The purified, white, crystallized hydrochloride has a melting point from 240° to 241° C.

Elementary analysis for $C_{11}H_{14}N_5Cl$ (MW 251.72):

|  | C (%) | H (%) | N (%) | Cl (%) |
|---|---|---|---|---|
| Calculated | 52.49 | 5.61 | 27.82 | 14.08 |
| Found | 52.48 | 5.80 | 28.0 | 14.16 |

Analogous to the methods described in Examples 1 to 4, the following compounds are produced:

| | M.P. |
|---|---|
| 6-(2-Imidazolin-2-yl-amino)-1-methyl-indazole dihydrochloride with | M.P. 247–249°; |
| 6-(2-Imidazolin-2-yl-amino)-2-methyl-indazole dihydrochloride with | M.P. 217–219°; |
| 7-(2-Imidazolin-2-yl-amino)-2-methyl-indazole dihydrochloride with | M.P. 170–171°; |
| 4-(2-Imidazolin-2-yl-amino)-1-benzyl-indazole with | M.P. 170–171°; |
| 4-(2-imidazolin-2-yl-amino)-2-benzyl-indazole with | M.P. 214–216°; |
| 5-(2-Imidazolin-2-yl-amino)-1-benzyl-indazole with | M.P. 173–174°; |
| 5-(2-Imidazolin-2-yl-amino)-1-(4-chloro-benzyl)-indazole with | M.P. 153–155°; |
| 5-(2-Imidazolin-2-yl-amino)-2-benzyl-indazole with | M.P. 186–189°; |
| 7-(2-Imidazolin-2-yl-amino)-1-benzyl-indazole with | M.P. 177–179°; |
| 7-(2-Imidazolin-2-yl-amino)-2-benzyl-indazole with | M.P. 180–182°; |
| 5-Chloro-1-(2-imidazolin-2-yl-amino)-phenyl)-indazole with | M.P. 186–188°; |
| 5-Chloro-1-(3,5-dichloro-4-(2-imidazolin-2-yl-amino)-phenyl)-indazole hydrochloride with | M.P. 333–334°; |
| 5-Chloro-1-(3,5-dichloro-2-(2-imidazolin-2-yl-amino)-phenyl)-indazole with and | M.P. 241–243° |
| 5-Chloro-1-(3-(2-imidazolin-2-yl-amino)-benzyl)-indazole with | M.P. 216–218° |

We claim:
1. 1H- and 2H-indazole derivative selected from the group consisting of 4-(2-imidazolin-2-ylamino)-2-ben- zyl-indazole, 6-(2-imidazolin-2-ylamino)-2-methyl-indazole dihydrochloride, 4-(2-imidazolin-2-ylamino)-1-benzyl-indazole, 5-(2-imidazolin-2-ylamino)-1-benzylindazole, 5-(2-imidazolin-2-ylamino)-1-(4-chlorobenzyl)-indazole, 5-(2-imidazolin-2-ylamino)-2-benzyl-indazole, 7-(2-imidazolin-2-ylamino)-1-benzyl-indazole, 7-(2-imidazolin-2-ylamino)-2-benzyl-indazole, 5-chloro-1-(2-imidazolin-2-ylamino)phenyl)-indazole, 5-chloro-1-(3,5-dichloro-4-(2-imidazolin-2-ylamino)phenyl)-indazole hydrochloride, 5-chloro-1-(3,5-dichloro-2-(2-imidazolin-2-ylamino)phenyl)-indazole, 5-chloro-1-(3-(2-imidazolin-2-ylamino)benzyl)-indazole or a pharmaceutically acceptable salt thereof.

2. The compound of claim 1 which is 4-(2-imidazolin-2-ylamino)-2-benzyl-indazole.

3. The compound of claim 1 which is 6-(2-imidazolin-2-ylamino)-2-methyl-indazole dihydrochloride.

4. The compound of claim 1 which is 4-(2-imidazolin-2-ylamino)-1-benzyl-indazole.

5. The compound of claim 1 which is 5-(2-imidazolin-2-ylamino)-1-benzyl-indazole.

6. The compound of claim 1 which is 5-(2-imidazolin-2-ylamino)-1-(4-chlorobenzyl)-indazole.

7. The compound of claim 1 which is 5-(2-imidazolin-2-ylamino)-2-benzyl-indazole.

8. The compound of claim 1 which is 7-(2-imidazolin-2-ylamino)-1-benzyl-indazole.

9. The compound of claim 1 which is 7-(2-imidazolin-2-ylamino)-2-benzyl-indazole.

10. The compound of claim 1 which is 5-chloro-1-(2-imidazolin-2-ylamino)phenyl)-indazole.

11. The compound of claim 1 which is 5-chloro-1-(3,5-dichloro-4-(2-imidazolin-2-ylamino)phenyl)-indazole hydrochloride.

12. The compound of claim 1 which is 5-chloro-1-(3,5-dichloro-2-(2-imidazolin-2-ylamino)phenyl)-indazole.

13. The compound of claim 1 which is 5-chloro-1-(3-(2-imidazolin-2-ylamino)benzyl)-indazole.

14. 1H- and 2H-indazole derivative of the formula

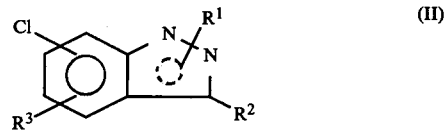

or a pharmaceutically acceptable salt thereof, wherein, in formula II

R1 represents hydrogen, a lower alkyl, a lower cyclic alkyl, phenyl, benzyl or chloro-benzyl group, bound to one or both nitrogen atoms in the 1 or 2 position, wherein the phenyl portion of the last three named groups may be substituted with an R4 group, R2 and R3 are the same or different from each other and represent halogen, an hydroxyl group, a lower alkyl group, a lower alkoxy group or a lower alkylthio group, and R4 represents a 2-imidazolin-2-yl-amino group.

15. The compound of claim 14 wherein said lower alkyl and said lower cyclic alkyl contain up to six carbon atoms.

16. The compound of claim 15 wherein said lower alkyl represents a saturated, branched or unbranched acyclic carbon chain of up to 4 carbon atoms in length.

17. The compound of claim 14 wherein the phenyl portion of the last three named R1 groups is substituted with chlorine.

* * * * *